United States Patent [19]
Hartigan et al.

[11] 4,083,702
[45] Apr. 11, 1978

[54] CHROMATOGRAPHIC COLUMN FITTINGS

[75] Inventors: Martin Joseph Hartigan, Huntington; Francis Paul Wilson, Oxford, both of Conn.

[73] Assignee: The Perkin-Elmer Corporation, Norwalk, Conn.

[21] Appl. No.: 706,897

[22] Filed: Jul. 19, 1976

[51] Int. Cl.² .............................................. B01D 15/08
[52] U.S. Cl. ........................................ 55/67; 55/386
[58] Field of Search .......................... 55/67, 197, 386; 285/156, 176, 177, 239, 242, 245

[56] References Cited

U.S. PATENT DOCUMENTS

| | | | |
|---|---|---|---|
| 2,985,291 | 5/1961 | Schoepe et al. | 285/177 X |
| 3,381,982 | 5/1968 | Elek | 285/177 X |
| 3,498,027 | 3/1970 | Buchtel, Jr. | 55/197 |
| 3,626,761 | 12/1971 | Haruki et al. | 55/197 X |
| 3,776,577 | 12/1973 | Dickey | 285/156 X |
| 3,880,452 | 4/1975 | Fields | 285/177 |

FOREIGN PATENT DOCUMENTS

2,301,749  7/1974  Germany .............................. 55/386

*Primary Examiner*—John Adee
*Attorney, Agent, or Firm*—S. A. Giarratana; F. L. Masselle

[57] ABSTRACT

A chromatographic column fitting for connecting the column to a connecting tube, which includes a union having an axial through-bore that includes at both ends thereof: a first portion, a second inwardly tapered portion, and a third cylindrical portion connecting the second portions of both ends; one end of the connecting tube being receivable in one end of the union and one end of the column tube being receivable in the other end of the union so that the end of the two tubes engage in butt-to-butt relationship; and ferrules wedged between the outside surfaces of the tubes and their adjacent second portions of the union, respectively; and in another form thereof the invention provides an outlet column fitting which includes a T-shaped union having an inlet at one end and an outlet at the other end and having an axial through-bore, which includes sequentially from the inlet to the outlet, a first inwardly tapered portion, a second cylindrical portion, a third manifold portion, the union having a side inlet opening into the manifold and the outlet end of the column tube being receivable in the inlet end of the union and extending through the first and second portions and into the manifold portion to a point toward the outlet end thereof so that make-up gas sweeps the outlet of the column tube, and a second connecting tube being connected to the outlet of the union.

16 Claims, 11 Drawing Figures

CHROMATOGRAPHIC COLUMN FITTINGS

BACKGROUND OF THE INVENTION

This invention relates to connecting unions, and more particularly to chromatographic column fittings. It is particularly adapted, among many other possible uses, for coupling the inlet and the outlet of a glass capillary column to the remainder of the system. It is also particularly applicable to metal capillary systems.

In the art of gas chromatography, it is conventional for a sample together with carrier gas to be injected into a glass capillary column where it is heated, and the effluent therefrom directed to one of various types of detectors, for analyzing the characteristics of the particular sample. Such instruments are very sensitive and, hence, the performance accuracy is of the utmost importance. Heretofore, difficulties were experienced with such instruments due to the inaccuracies resulting from conventional fittings used for the connections to and from the glass capillary column. It will be appreciated that in many installations glass lined stainless steel tubing of relatively large diameter, such as about 1.59 mm. outside diameter for example, is coupled to a glass capillary column of relatively small diameter, such as about 0.75 mm. outside diameter for example. It should also be appreciated that the sample size in such installations is relatively small, thereby compounding the difficulties involved. Conventional fittings including so-called "zero dead volume" types caused degradation of the column performance, particularly with respect to loss of column efficiency and degradation of the peak shape, such as tailing, in the chromatogram.

Our invention involves a novel combination of features combined in such a way as to afford a very efficient and effective solution to the deficiencies encountered with the prior art, as will become apparent as the description proceeds.

SUMMARY OF THE INVENTION

In order to accomplish the desired results we provide, in one form of the invention, a new and improved chromatographic column fitting for interconnecting a column tube with a connecting tube, which includes a union member having an axial through-bore. This through-bore includes, at both ends thereof, a first portion, a second inwardly tapered portion connected to the first portion, and a third cylindrical portion that connects the second portion of one end with the second portion of the other end. One end of the connecting tube is receivable in one end of the union and one end of the column tube is receivable in the other end of the union so that it engages the end of the connecting tube in butt-to-butt relationship. Further, ferrules are wedged between the outside surfaces of the two tubes and their adjacent second portions of the union to retain the tubes in the union, and thereby provide essentially a ferrule-to-ferrule orientation to eliminate dead volume.

According to one aspect of the invention, the column tube is a glass capillary tube and the connecting tube is a glass lined stainless steel tube, which has a substantially greater outside diameter than the outside diameter of the glass capillary tube.

Our invention provides, in another form thereof, a new and improved chromatographic column fitting for the outlet of a chromatographic column, which is characterized by a T-shaped union having an inlet at one end an outlet at the other end thereof, and an axial through-bore. This through-bore includes, sequentially from the inlet to the outlet, a first inwardly tapered portion, a second cylindrical portion connected to the first portion, a third elongated cylindrical manifold portion connected to the second portion, and a fourth tapered portion. The union member has a side inlet opening into the manifold portion for receiving make-up gas. The outlet of the column tube is receivable in the inlet end of the union and extends through the first and second portions and into the manifold portion to a point towards the outlet end thereof, with respect to the opening of the side inlet so that make-up gas sweeps the outlet of the column tube to minimize the dead volume of the connection and effectively eliminate the extra-column volume in the manifold. In addition, means are provided for coupling a connecting tube to the outlet of the union member. It will be appreciated that according to an aspect of this invention the column tube may be a glass capillary tube.

DETAILED DESCRIPTION OF THE PREFERRED EMBODIMENT

Figure 1:
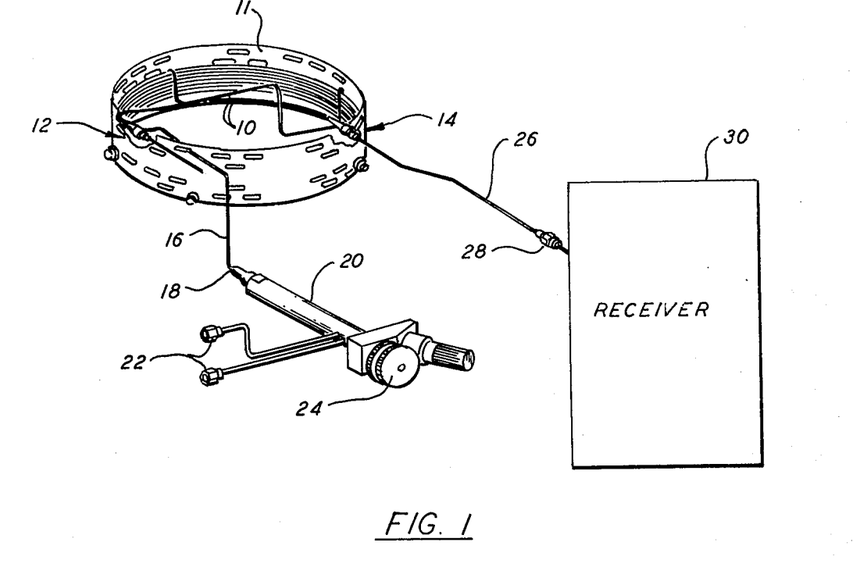
FIG. 1 is a partial schematic and partial pictorial view of a portion of a gas chromatograph showing an all-glass capillary system.

In FIG. 1 there is shown a partial schematic and partial pictorial view of a portion of a gas chromatograph comprising a glass capillary column 10 having an inlet fitting or connecting union indicated at 12 and an outlet fitting or connecting union indicated at 14. A cage 11 is provided which makes it possible to connect the columns to the cage without straightening the column ends and provides relatively rugged fittings for the cage and column installation. The inlet connecting union 12 receives one end of a glass lined stainless steel tube 16 and the other end thereof is coupled, as at 18, to an injector assembly 20, which includes inlets 22 for receiving carrier gas and a septum cap 24 through which the sample is introduced into the system. The outlet connecting union 14 receives one end of a glass lined stainless steel tube 26 and the other end thereof is coupled, as at 28, to a receiver 30 of a detector assembly. In operation, the carrier gas flows from the injector 20 through the glass capillary column 10 and thence to the receiver 30. Periodically a sample is added to the carrier gas in the injector and thence injected into the column where it may be heated before passing to the receiver of the detector assembly for analysis of its characteristics.

Figure 2:
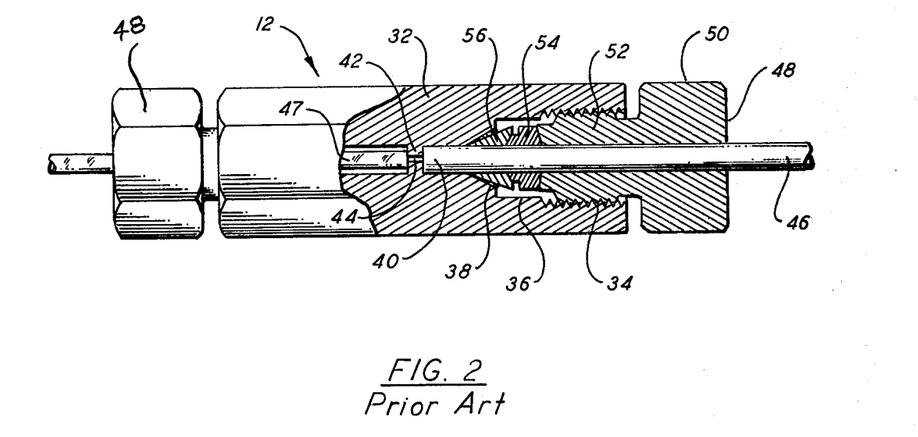
FIG. 2 is an enlarged, medial sectional view of a fitting according to the prior art.

FIG. 2 shows a conventional inlet fitting or connecting union that comprises a union member 32 having an axial through-bore, which includes at both ends thereof, a first cylindrical portion 34 with internal threads, a second cylindrical portion 36, a third inwardly tapered portion 38, and a fourth cylindrical portion 40. At about the center of the union there is a radially inwardly projecting ring portion 42 having a medial, straight through-bore 44. This ring portion forms an axial shoulder or seat against which the end of a glass lined stainless steel tube 46 abuts. This tubing has, for example, an outside diameter of about 1.59 mm. It is particularly noted that the other side of the ring portion 42 forms another shoulder or seat against which the end of the glass capillary tubing 47 of the column abuts. This tubing has, for example, an outside diameter of about 0.75 mm. Thus, the ends of these two tubes are spaced apart from each other by the thickness of this ring portion 42. The glass lined stainless steel tubing is held in position by means of a tightening member 48 having a hexagonal head portion 50 for adjustment purposes and a projecting portion 52 having external threads which mate with the internal threads 34. Axial movement of this member causes the end thereof to engage a cylindrical spacer 54 that, in turn, engages an inwardly tapered Vespel ferrule 56, the inner end of which wedges between the inwardly tapered portion 38 of the union and the outside of the glass lined stainless steel tubing 46 to thereby retain the tubing in the union. The glass capillary tubing is maintained in the union in the same manner at the other end thereof. It has been found that this prior art construction causes degradation of the peak shape and loss of column efficiency when used to connect two pieces of tubing with such a large variation in their diameters, as will be discussed more fully hereinafter.

Figure 3:
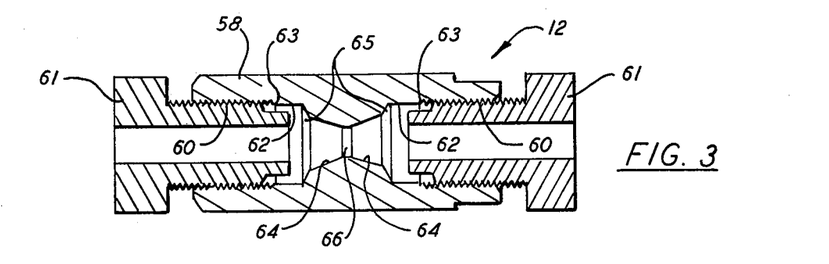
FIG. 3 is an enlarged, medial sectional view of a chromatographic column fitting constructed in accordance with the concepts of the present invention.
Figure 4A:
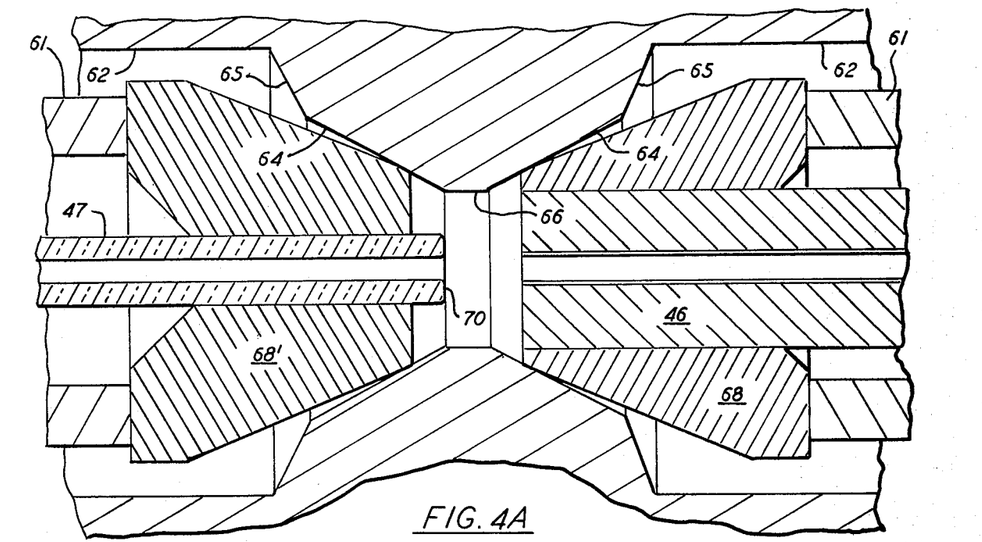
FIGS. 4A, 4B and 4C are enlarged, fragmentary medial sectional views of the fitting of FIG. 3, showing the steps of the assembly of the tubings therein.
Figure 4B:
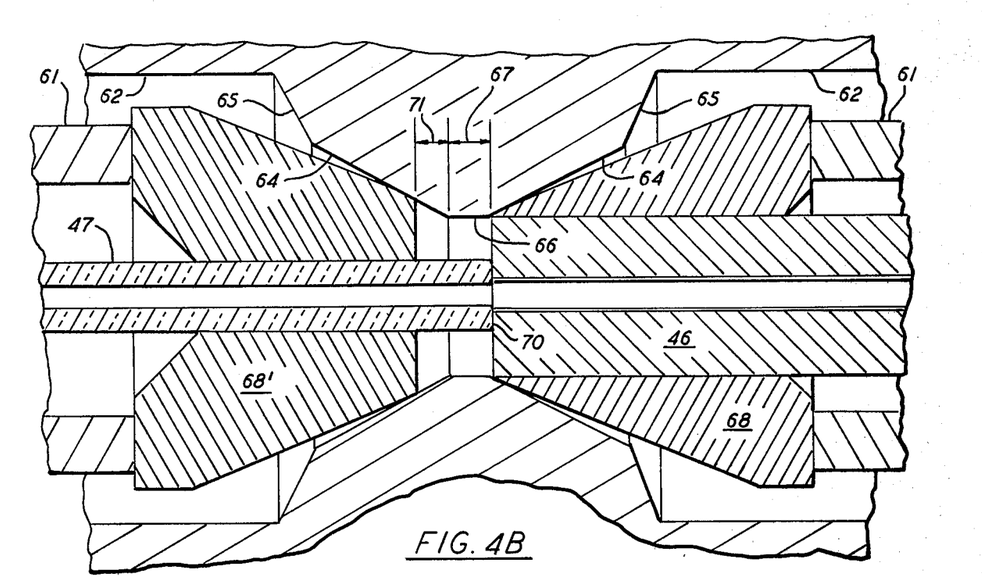
Figure 4C:
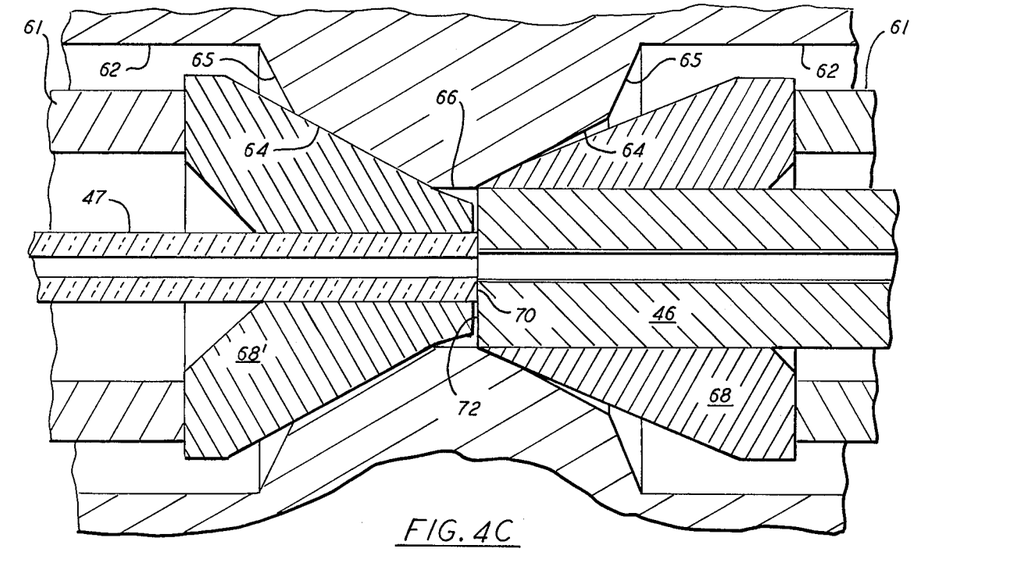

In the embodiment of the invention illustrated in FIGS. 3 and 4, the inlet fitting or connecting union 12 comprises a union member 58 having an axial through-bore which includes at both ends thereof, a first cylindrical portion having a part 60 thereof provided with internal threads for receiving an internal tightening nut 61, and another part 62 connected to the first part with a chamfer 63, a second inwardly tapered portion 64 connected to the first portion by a chamfer 65, and a third central cylindrical portion 66 connecting the second portion of one end of the union with the second portion of the other end of the union. The length of this cylindrical portion, as indicated at 67 in FIG. 4B, is of the order of about 0.026 inches, for example, when employing tubes of the aforementioned dimensions.

FIGS. 4A, 4B and 4C show the steps employed in the assembly of the glass capillary tubing 47 and the glass lined stainless steel tubing 46 in the connecting union 12, according to the invention. Initially, as illustrated in FIG. 4A, the glass lined tubing 46 together with its associated tapered polymeric or Vespel ferrule 68 are inserted into one end of the union until the ferrule 68 engages the second inwardly tapered portion 64, and the glass capillary tubing 47 together with its associated tapered polymeric or Vespel ferrule 68' are inserted into the other end of the union until the ferrule 68' engages the other second inwardly tapered portion 64. At this time the two Vespel ferrules 68 and 68' are in their noncompressed positional relationships.

Next, as seen in FIG. 4B, the Vespel ferrule 68 together with the glass lined stainless steel tubing 46 is urged inwardly by means of the internal nut 61 until the inner ends thereof reach the intersection of the third central cylindrical portion 66 and the second inwardly tapered portion 64. Then, the glass capillary tubing 47 is urged inwardly until the end thereof 70 engages the end of the glass lined stainless steel tubing 46 in butt-to-butt relationship, while the Vespel ferrule 68' remains stationary. At this time the Vespel ferrule 68 is in its compressed state and the Vespel ferrule 68' is in its noncompressed condition, the distance between the end of the ferrule 68' and the intersection of the third central cylindrical portion 66 with the second inwardly tapered portion 64, as indicated at 71 in FIG. 4B, is of the order of about 0.016 inches, for example, when employing tubing of the aforementioned dimensions. Finally, as seen in FIG. 4C, the Vespel ferrule 68' is urged inwardly and compressed by means of the internal nut 61 until the end thereof is essentially in a ferrule-to-ferrule relationship with respect to the end of the ferrule 68, as indicated at 62. It is noted that in their assembled positions, the glass lined tubing 46 is held in position by means of the wedging effect of the Vespel ferrule between the outside surface of the tubing and the inwardly tapered portion 64, and the glass capillary tubing 47 is held in position by means of the wedging effect of the Vespel ferrule between the outside surface thereof and its corresponding inwardly tapered portion 64. In view of the fact that the glass capillary tubing has an outside diameter of about 0.75 mm., whereas the outside diameter of the glass lined stainless steel tubing is about 1.59 mm., for example, the Vespel ferrule 68' is slightly thicker than the ferrule 68, and in view of the structural characteristics of the two tubes, the compression of the ferrule 68 is greater than the compression of the ferrule 68'.

It will be particularly appreciated that with this structure the end 70 of the glass capillary tube 47 and the end of the glass lined stainless steel tubing 46 form a butt-to-butt union, and that when using polymeric ferrules, there is essentially a ferrule-to-ferrule orientation, which eliminates dead volume.

Figure 5:
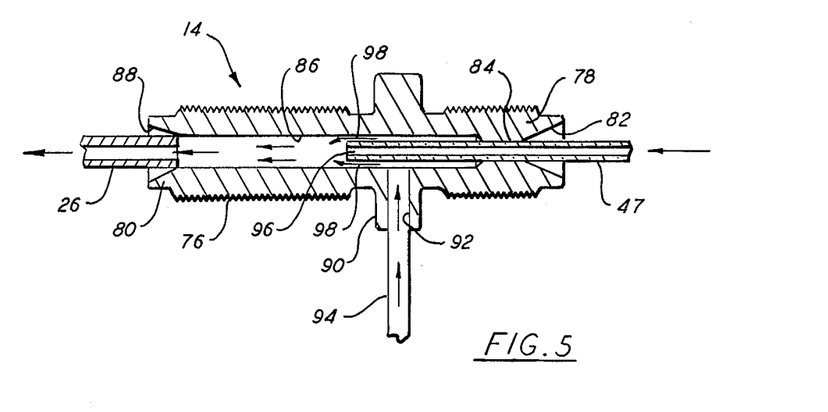
FIG. 5 is an enlarged, medial sectional view of a chromatographic column fitting according to another embodiment of the invention.

In the embodiment of the invention illustrated in FIG. 5, the column outlet fitting or connecting union 14 comprises a T-shaped union member 76 having an inlet end 78 connected to the glass capillary column 10 and an outlet end 80 connected to the glass lined stainless steel tubing 26 leading to the receiver. The union 76 has an axial through-bore which includes sequentially from the inlet to the outlet, a first inwardly tapered position 82, a relatively short second cylindrical portion 84 connected to the first portion, a third elongated cylindrical manifold portion 86 connected to the second portion by a chamfer, and a fourth outwardly tapered portion 88. The union 76 is provided with a side inlet boss 90 having a bore therein 92 for receiving a make-up gas tube 94. This bore opens into the manifold portion 86. The diameter of the second cylindrical bore 84 is substantially the same as the outside diameter of the glass capillary tubing 47 for forming a relatively tight, interference fit therebetween. When assembled, the capillary tubing 47 is arranged to pass through the first and second portions 82 and 84 into the manifold portion 86 so that the end 96 thereof extends slightly beyond the opening of the make-up gas tube 94. In operation, the make-up gas, as indicated by the arrows 98, sweeps the end 96 of the glass capillary tube 47, thereby minimizing the dead volume of the connection and effectively eliminates the extra-column volume in the manifold portion 86. The fourth outwardly tapered portion 88 receives the end of the glass lined stainless steel tubing 26 for passing the gas and sample to the receiver, FIG. 1.

The following examples will illustrate the effectiveness of the chromatographic column connecting fittings of the present invention. The tests were conducted using a 25 meter Carbowax 20M column, as manufactured by the Perkin-Elmer Corporation. This is a relatively short, low volume column, and consequently, emphasizes the effect of extra-column and unswept dead volumes. Isothermal operating conditions were used, as temperature programming can mask the effect of poor conditions. The test sample used was a high temperature polarity test mix consisting of nonane, ispropyl benzene, cyclohexanone, and hexanol −1. This mixture is useful in pointing up dead volume problems via the hydrocarbon peak shape and the activity by the alcohol and ketone peak shapes. Any tailing evident in the chromatogram can be identified as to its source with this sample. The chromatographic test conditions were, as follows:

| | |
|---|---|
| Oven Temp. | 105° C |
| Injection Temp. | 250° C |
| Det. Temp. | 250° C |
| Splitter 221:1 | 100 cc/min. precolumn 0.45 cc/min. analytical col. |
| Sample size | 0.2 ul. |
| Attenuation | 256X; Chart Speed 10 mm/min. |

EXAMPLE 1

Figure 6:
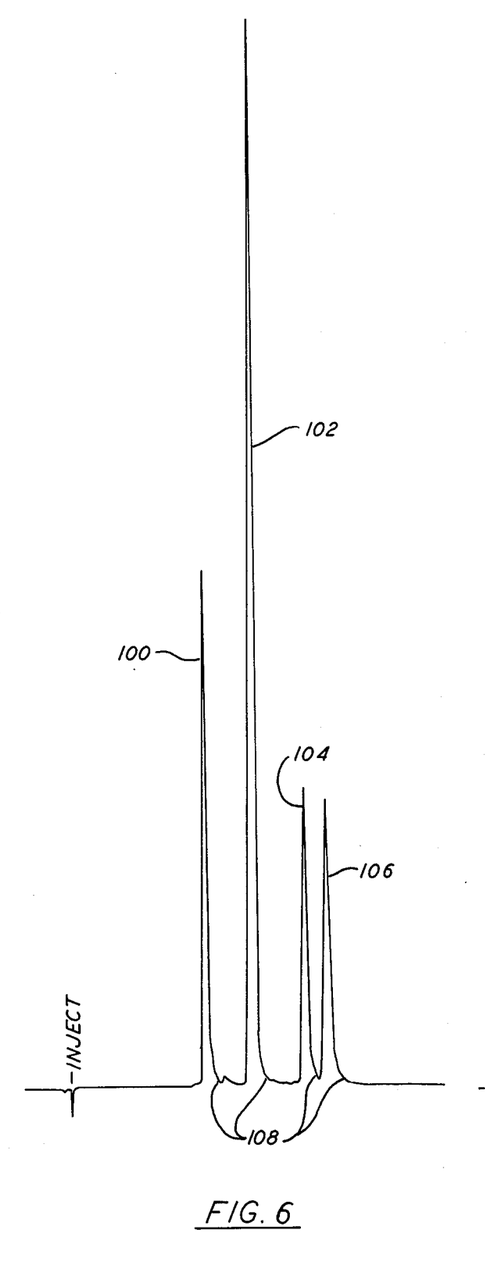
FIG. 6 is a graphic illustration of a chromatogram showing the performance of a system using a conventional prior art fitting at the glass capillary column outlet.

As a testing expediency, the column was inserted directly into the injector (which acted as the split point), in order to eliminate the column inlet fitting from consideration, for purposes of testing the column outlet fitting. A conventional low volume outlet fitting and a glass lined stainless steel tube were used to connect the column to the receiver. The results of this test run are illustrated in the chromatogram of FIG. 6, the order of elution being; nonane as indicated at 100, isopropylbenzene at 102, cyclohexanone at 104, and hexanol −1 at 106. It will be appreciated that there is some tailing, as indicated at 108, on all of the peaks, which is evidence of unswept dead volume. The unswept volume was found to be in the union connecting the glass capillary column to the glass lined stainless steel tubing.

EXAMPLE 2

Figure 7:
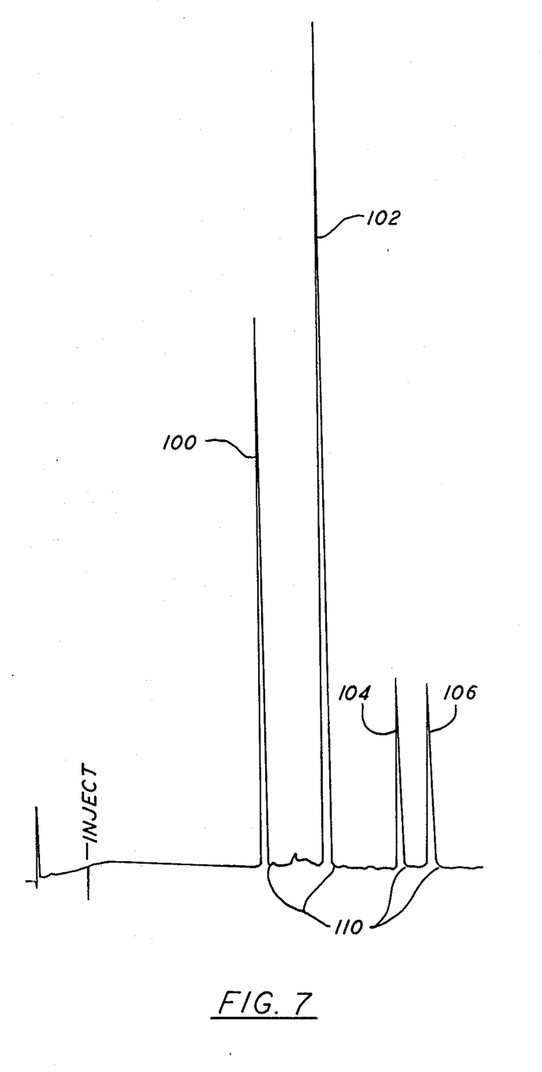
FIG. 7 is an illustration similar to FIG. 6, but showing the performance of the system using a fitting according to the present invention at the column outlet.

The conditions of the test of example 2 were the same as for example 1, except that Applicants' outlet fitting or connecting union 14, as shown in FIG. 5, was substituted for the conventional fitting of example 1. The results of this test run are illustrated in the chromatogram of FIG. 7, the order of elution being the same as indicated in example 1. It will be appreciated that there is substantially no evidence of dead volume tailing, as indicated at 110 in FIG. 7. Further, there is no evidence of band broadening. The make-up gas sweeps the end of the column minimizing the dead volume of the connection and effectively eliminates the extra-column volume in the glass lined tubing manifold.

EXAMPLE 3

Figure 8:
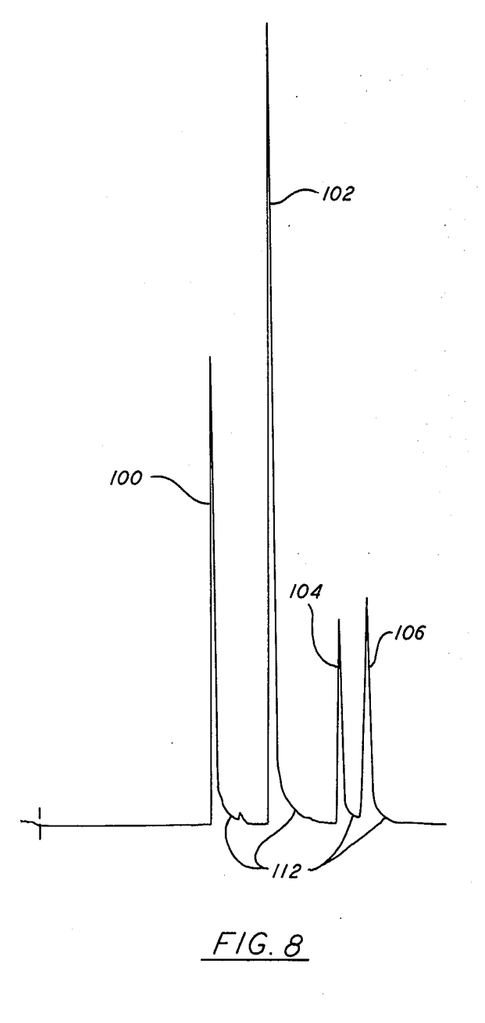
FIG. 8 is an illustration similar to FIG. 7, but showing the performance of the system using a conventional prior art fitting at the column inlet.

In view of the fact that a cage was used in conjunction with the column, two fittings were required, one at the column inlet and one at the column outlet. The conditions of the test of example 3 were the same as for example 2, except that at the column inlet a glass lined stainless steel split point was employed, which was connected to the glass capillary column by a conventional union. The results of this test run are illustrated in the chromatogram of FIG. 8, the order of elution being the same as indicated in sample 2. As indicated at 112, both the peak shape and efficiency suffered dramatically due to this addition.

Several modifications were attempted in order to eliminate the unwanted volume, but they were not very satisfactory. The glass lined tube was wrapped with Teflon tape prior to insertion into the union. The tape filled the volume and helped alleviate the problem to some extent, but it was not too satisfactory because it was very difficult to get the proper thickness of tape and, therefore, very dependant on technique. Next, graphite ferrules were substituted for the Vespel ferrules of the conventional union. The soft graphite deformed under the pressure of tightening the fitting and filled the void volume in the union. This improved the performance of the system, but was found to be impractical because it destroyed the ferrule so that it could only be used once. In addition, the graphite ferrules posed another problem in that they frequently leaked due to the small diameter (0.75 mm.) of the glass capillary tubing.

EXAMPLE 4

Figure 9:
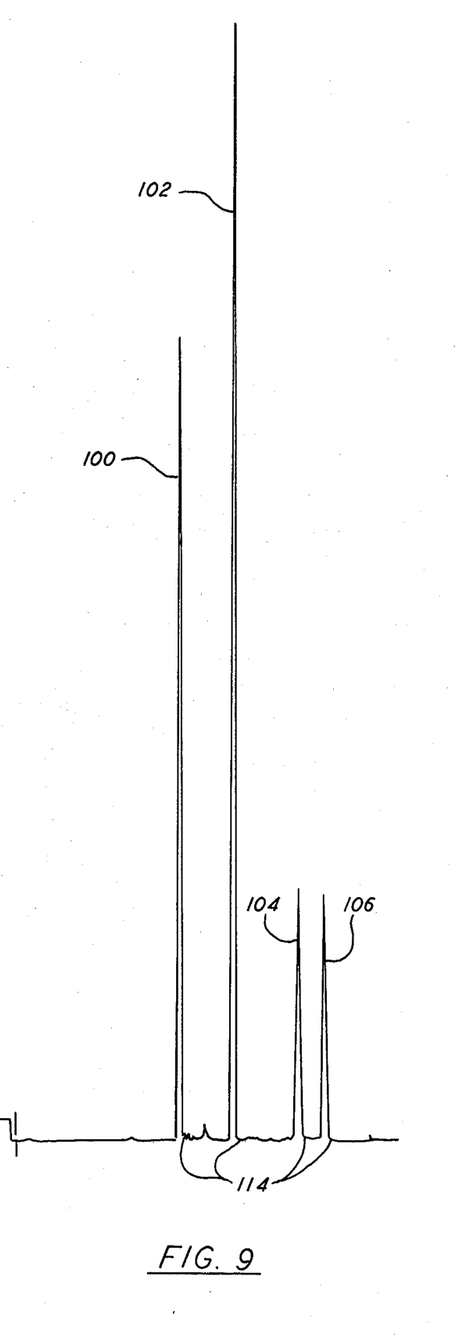
FIG. 9 is an illustration similar to FIG. 8, but showing the performance of the system using a fitting according to the invention at the column inlet.

The conditions of the test of example 4 were the same as for example 3, except that Applicants' inlet fitting or connecting union 12, as shown in FIGS. 3, 4A, 4B and 4C, was substituted for the conventional fitting of example 3. The results of this test run are illustrated in the chromatogram of FIG. 9, the order of elution being the same as that indicated in example 3. It will be particularly appreciated that, as indicated at 114 in the chromatogram, there is no evidence of dead volume tailing or band broadening.

Thus, improved chromatographic column fittings have been shown. Although specific embodiments have been illustrated and described, it will be obvious to those skilled in the art that various modifications may be made without departing from the spirit of the invention, which is intended to be limited solely by the appended claims.

What is claimed is:

1. In a chromatograph having a chromatographic column tube and a connection tube, a fitting for interconnecting said tubes comprising:
   a union member having an axial through-bore which includes at both ends thereof;
   a first portion,
   a second inwardly tapered portion connected to the first portion, and
   a third cylindrical portion connecting the second portion of one end of the union member with the second portion of the other end of the union member;
   one end of said connecting tube being receivable in one end of said union member and one end of said column tube being receivable in the other end of said union member, said one end of said connecting tube and said one end of said column tube being engageable in butt-to-butt relationship within said union member, means for wedging ferrule means between the outside surface of said connecting tube and the adjacent second portion of said union member to retain said connecting tube in said union member, and means for wedging second ferrule means between the outside surface of said column tube and the adjacent second portion of said union member to retain said column tube within said union member, the adjacent ends of the two ferrule means being disposed in essentially ferrule-to-ferrule orientation with respect to each other within said union member, and the two ferrule means extending substantially to the ends of the tubes respectively.

2. A chromatographic column fitting according to claim 1 wherein said one end of said column tube is the inlet end of said chromatographic column.

3. A chromatographic column fitting according to claim 1 wherein said first portion of said axial through-bore is cylindrical and part thereof has internal threads for receiving internal tightening nuts for wedging said ferrule means, respectively.

4. A chromatographic column fitting according to claim 1 wherein said first and second portions of said axial through-bore of said union member are connected by a chamfer.

5. A chromatographic column fitting according to claim 1 wherein said ferrule means are tapered polymeric ferrules.

6. In a chromatograph having a chromatographic column tube and a connecting tube, a fitting for interconnecting said tubes comprising:

a union member having an axial through-bore which includes at both ends thereof;
a first portion,
a second inwardly tapered portion connected to the first portion, and
a third cylindrical portion connecting the second portion of one end of the union member with the second portion of the other end of the union member;
one end of said connecting tube being receivable in one end of said union member and one end of said column tube being receivable in the other end of said union member, said one end of said connecting tube and said one end of said column tube being engageable in butt-to-butt relationship within said union member, said ends of said tubes engaging each other adjacent the intersection of the second inwardly tapered portion and the third cylindrical portion, at the end of the union member receiving the connecting tube,
means for wedging ferrule means between the outside surface of said connecting tube and the adjacent second portion of said union member to retain said connecting tube in said union member, and means for wedging second ferrule means being the outside surface of said column tube and the adjacent second portion of said union member to retain said column tube within said union member.

7. A chromatographic column fitting according to claim 6 wherein the location of said ferrule-to-ferrule orientation of the two ferrule means and the location of the engagement of the ends of the two tubes are adjacent each other.

8. A chromatographic column fitting according to claim 7 wherein said column tube is a glass capillary tube and said connecting tube is a glass lined stainless steel tube.

9. A chromatographic column fitting according to claim 8 wherein the outside diameter of said glass lined stainless steel tube is substantially greater than the outside diameter of said glass capillary tube.

10. In a chromatograph having a chromatographic column tube and a connecting tube, a fitting for interconnecting said tubes comprising:

a union member having an axial through-bore which includes at both ends thereof;
a first portion,
a second inwardly tapered portion connected to the first portion, and
a third cylindrical portion connecting the second portion of one end of the union member with the second portion of the other end of the union member;
one end of said connecting tube being receivable in one end of said union member and one end of said column tube being receivable in the other end of said union member, said one end of said connecting tube and said one end of said column tube being engageable in butt-to-butt relationship within said union member,
means for wedging ferrule means between the outside surface of said connecting tube and the adjacent second portion of said union member to retain said connecting tube in said union member, and means for wedging second ferrule means between the outside surface of said column tube and the adjacent second portion of said union member to retain said column tube within said union member,
said one end of said column tube being the inlet end of said chromatographic column, and the apparatus further including a second connecting tube, and a second fitting which comprises:
a T-shaped union member having an inlet at one end and an outlet at the other end thereof, said T-shaped union member having an axial through-bore which includes sequentially from the inlet to the outlet;
a first inwardly tapered portion,
a second cylindrical portion connected to the first portion, a third elongated cylindrical manifold portion connected to the second portion, and
a fourth outwardly tapered portion;
said T-shaped union member having side inlet means opening into said manifold portion for receiving make-up gas;
the outlet end of said column tube being receivable in the inlet end of said union member and extending through said first and second portions and into said manifold portion to a point towards the outlet end thereof with respect to the opening of said side inlet means so that make-up gas sweeps the outlet end of the column tube; and
means for connecting the second connecting tube to the outlet of said T-shaped union member.

11. Apparatus according to claim 10 wherein said column tube is a glass capillary tube and the first mentioned connecting tube is a glass lined stainless steel tube.

12. Apparatus according to claim 11 wherein the outside diameter of said glass lined stainless steel tube is substantially greater than the outside diameter of said glass capillary tube.

13. In a chromatograph having a chromatographic column tube and a connecting tube, a fitting for interconnecting the outlet of said column tube with one end of said connecting tube comprising:
- a T-shaped union member having an inlet at one end and an outlet at the other end thereof, said union member having an axial through-bore which includes sequentially from the inlet to the outlet;
- a first inwardly tapered portion,
- a second cylindrical portion connected to the first portion
- a third elongated cylindrical manifold portion connected to the second portion, and
- a fourth outwardly tapered portion;
- said union member having side inlet means opening into said manifold portion for receiving make-up gas;
- the outlet end of said column tube being receivable in the inlet end of said union member and extending through said first and second portions and into said manifold portion to a point towards the outlet end thereof with respect to the opening of said side inlet means so that make-up gas sweeps the outlet end of the column tube; and
- means for connecting the connecting tube to the outlet of said union member.

14. A chromatographic column fitting according to claim 13 wherein said column tube is a glass capillary tube.

15. A chromatographic column fitting according to claim 13 wherein said second cylindrical portion has a diameter substantially equal to the outside diameter of the column tube for receiving the column tube with an interference fit therebetween.

16. In a chromatograph having a chromatographic glass capillary column tube, a glass lined connecting tube and a fitting for interconnecting said tubes, said fitting comprising a union member having an axial through-bore which includes at both ends thereof; a first portion, a second inwardly tapered portion connected to the first portion, and a third cylindrical portion connecting the second portion of one end of the union member with the second portion of the other end of the union member; a method of assembling said fitting comprising the steps of:
- inserting into one end of said union member one end of the glass lined tube together with an associated tapered polymeric ferrule until the ferrule engages the adjacent second inwardly tapered portion, and inserting into the other end of said union member one end of the glass capillary tube together with an associated tapered polymeric ferrule until the ferrule engages its adjacent second inwardly tapered portion; and thence
- urging the glass lined tube with its associated ferrule inwardly and compressing said ferrule until both the inner end of the glass lined tube and the inner end of the ferrule reach the intersection of the third cylindrical portion and the adjacent second tapered portion, and then urging the glass capillary tube inwardly until the end thereof engages the end of the glass lined tube in butt-to-butt relationship; and thence
- urging inwardly and compressing the ferrule associated with the glass capillary tube until the inner end of the ferrule extends substantially to the inner end of the glass capillary tube to form an essentially ferrule-to-ferrule relationship with respect to the end of the ferrule associated with the glass lined tube; whereby
- said tubes are held in position by means of the wedging effect of the ferrules between the outside surfaces of the tubes and the second inwardly tapered portions, respectively.

* * * * *